United States Patent
Baginksi et al.

(10) Patent No.: US 6,499,876 B1
(45) Date of Patent: Dec. 31, 2002

(54) MONITORING APPARATUS

(75) Inventors: Edward Baginksi, Sharnbrook (GB); Ian William Burns, Sharnbrook (GB); Anthony Peter Hasting, Sharnbrook (GB)

(73) Assignee: JohnsonDiversey, Inc., Sturtevant, WI (US)

(*) Notice: Subject to any disclaimer, the term of this patent is extended or adjusted under 35 U.S.C. 154(b) by 0 days.

(21) Appl. No.: 09/359,010

(22) Filed: Jul. 22, 1999

(30) Foreign Application Priority Data

Jul. 22, 1998 (EP) .............................. 98305846

(51) Int. Cl.[7] .................... G01N 25/00; G01K 17/00
(52) U.S. Cl. ............................. 374/7; 374/29
(58) Field of Search ................. 374/4, 5, 6, 7, 374/45, 120, 29, 147

(56) References Cited

U.S. PATENT DOCUMENTS

| | | | | |
|---|---|---|---|---|
| 3,217,538 A | * | 11/1965 | Loeb ........................... | 374/29 |
| 3,367,182 A | * | 2/1968 | Baxter ......................... | 374/29 |
| 3,453,865 A | * | 7/1969 | Blanchard et al. ............ | 374/29 |
| 3,720,103 A | * | 3/1973 | Adams et al. ............. | 73/190 H |
| 3,810,009 A | * | 5/1974 | Hausler et al. ................ | 374/7 |
| 3,913,378 A | * | 10/1975 | Hausler ...................... | 73/15 R |
| 4,024,751 A |   | 5/1977 | Potrzebowski | |
| 4,176,544 A |   | 12/1979 | Eyles et al. | |
| 4,383,438 A |   | 5/1983 | Eaton | |
| 4,396,300 A | * | 8/1983 | Characklis et al. ........... | 374/43 |
| 4,486,743 A | * | 12/1984 | Brown ......................... | 374/45 |
| 4,722,610 A | * | 2/1988 | Levert et al. ................. | 374/29 |
| 4,923,306 A | * | 5/1990 | Fauske ......................... | 374/34 |
| 4,988,210 A | * | 1/1991 | Koshihara et al. ............. | 374/5 |
| 5,171,518 A |   | 12/1992 | Barshay et al. | |
| 5,399,017 A | * | 3/1995 | Droege .......................... | 374/7 |
| 5,590,706 A | * | 1/1997 | Tsou et al. .................. | 165/11.1 |
| 5,645,348 A | * | 7/1997 | Stulen et al. ................. | 374/45 |
| 6,257,761 B1 | * | 7/2001 | Chuah et al. ................. | 374/45 |

FOREIGN PATENT DOCUMENTS

| | | | |
|---|---|---|---|
| GB | 2 089 512 | 9/1981 | |
| JP | 55010510 A | * 1/1980 | .................. 374/29 |
| JP | 61026809 A | * 2/1986 | .................. 374/45 |
| JP | 03197856 A | * 8/1991 | .................. 374/45 |
| WO | 92/15866 | 9/1992 | |

OTHER PUBLICATIONS

The Use of Heat Flux Sensor in Monitoring Fouling, Jones et al., pp. 230–241 (1994).

* cited by examiner

Primary Examiner—Christopher W. Fulton
Assistant Examiner—Mirellys Jagan
(74) Attorney, Agent, or Firm—Warren R. Bovee; Neil E. Hamilton; Renee R. Rymarz

(57) ABSTRACT

A monitoring apparatus (1) for monitoring soil build-up in a pipe (6) which may form part of a pipework system including a heat exchanger. The pipework system is used in e.g. the heat treatment of milk and milk products. The monitoring apparatus (1) is in thermal connection with the pipe (6) and includes a body (2) capable of being heated by a heater. The power supplied to the heater is controlled and monitored such that a change in power input to the heater is indicative of a change in heat transfer to a fluid (8) flowing through the pipe (6). The heat from the apparatus (1) causes localized soil build-up in a portion of the pipe (6) near to the heated body (2). The soil build-up is representative of the soil build-up in the heat exchanger. The cleaning of the pipe (6) may be based on the soil build-up indicated by the monitoring apparatus (1).

4 Claims, 4 Drawing Sheets

Figure 1:
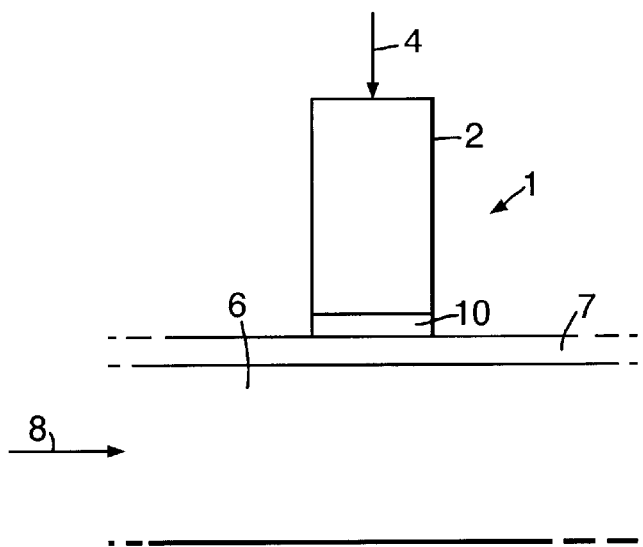

Block 150C bulk 75C
Metal thickness 1mm
Product film coefficient 2000 W/m^2K

Even fouling within heat exchanger

Uneven fouling within heat exchanger

MONITORING APPARATUS

FIELD OF THE INVENTION

The present invention relates to monitoring apparatus and in particular to monitoring apparatus for use in monitoring soil build-up in a pipework system which includes a heat exchanger.

BACKGROUND OF THE INVENTION

The monitoring apparatus of the present invention is particularly though not exclusively suitable for use in processes involved with the heat treatment of milk and milk products. The soil build-up in the conduits of heat treatment equipment for milk and milk products is a serious problem, threatening the sterile operation of the equipment and reducing the efficiency of the process. Frequent cleaning is often necessary to remove deposits: often one shift in three is spent cleaning.

The use of a heat flux sensor to monitor fouling is known from a paper entitled "The use of a heat flux sensor in monitoring fouling" by A. D. Jones et al which forms part of the proceedings of a conference held at Jesus College, Cambridge, 23–25 March 1994, pages 230–241; edited by Fryer, Hasting and Jeurnink and published by the European Commission DGXII, Science, Research and Development (ISBN92-827-4360-8).

The heat flux sensor is intended to be used in processes involved with the heat treatment of milk and milk products. It was operated by attaching it to a pipe through which a milk protein solution flowed to represent the soil build-up that occurs when the milk protein solution is heated in a heat exchanger.

The heat flux sensor used by Jones et al measured heat flux alone to monitor the condition of the interior surface of the pipe. The sensor, which was a commercial heat flux sensor was used to measure a temperature difference across a known thermal resistance and from this the heat flux and heat transfer coefficient was calculated. The type of sensor used was a Rhopoint type 20450-2 and a number of points arise from the use of any such commercial type of heat flux sensor.

Firstly, a nanovoltmeter is used to measure a voltage corresponding to the temperature difference across the sensor. In the case of the sensor used by Jones et al the voltages measured were of the order of 400 to 1000 microvolts. These result in relatively low levels of sensor response, which might be feasible in a laboratory environment, but may well result in a significant noise-to-signal ratio if the sensor were to be used in a commercial environment. It can be see from the Hones et al paper that for a constant Reynolds number and bulk temperature, the heat transfer coefficient for the clean condition at time 0 varies considerably, e.g. between 0.21 and 0.31. This demonstrates the problems encountered when trying to ensure such small signals.

Secondly, it can be seen that the sensitivity of the system is limited by the heat flux element itself. Considering the Jones et al sensor arrangement, a 1 mm soil deposit would result in a theoretical reduction in the output signal of approximately 40–50%, i.e. a 2:1 attenuation. If the relative contribution of the thermal resistance of the heat flux sensor to the overall thermal resistance between the copper block and the bulk fluid is calculated, it is found that this accounts for 50–80%, i.e. the bulk of the heat transfer resistance. Thus the sensitivity of the system is limited by the heat flux element itself. Ideally, the limitation on overall heat transfer should be on the product side such that changes in the product side due to soil build-up have the maximum impact on sensor response.

Thirdly, the Jones et al paper does not take account of potential heat losses and their impact on the results obtained.

Figure 7A:
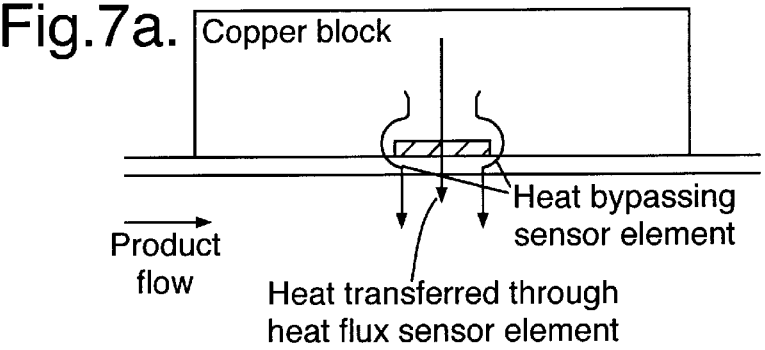
Figure 7B:
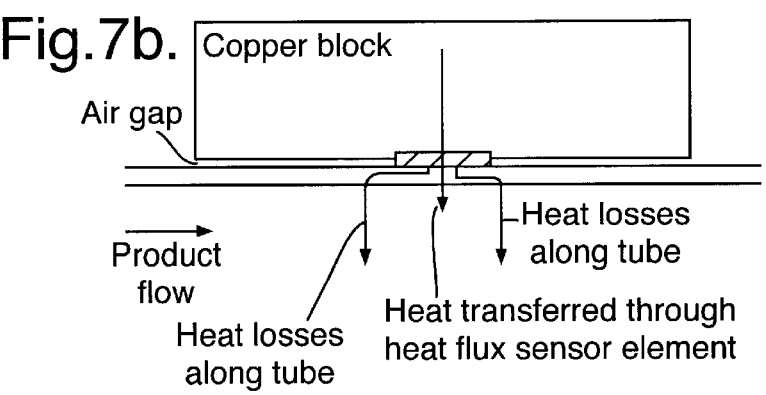

It can be seen from FIGS. 7a and 7b that in the heat flux sensing apparatus used by Jones et al there is a potential for heat to be lost. FIG. 7a shows that heat can be transferred from the copper block to the fluid conduit which by passes the heat flux element due to the heat energy taking the path of least resistance. Thus this heat loss is not considered. Another potential loss is shown in FIG. 7b and occurs if the copper block does not fully contact the fluid conduit. That is to say, if there is a small air gap between the copper block and the fluid conduit, there will be flow of heat along the conduit away from the heat flux element. The heat flux calculations shown are based on one dimensional heat transfer across the sensor element. The potential for heat losses indicated above invalidates these calculations.

With the known geometry of the heat flux sensing apparatus used by Jones et al and using standard heat transfer correlations for laminar flow heat transfer together with the heat flux element data, it is possible to calculate a predicted heat transfer coefficient. The predicted value of this for the Jones et al system is 0.65 kW/m²□K. This is substantially higher than the value mentioned by Jones et al and may well be a result of heat from the copper block by-passing the heat flux element.

Figure 6:
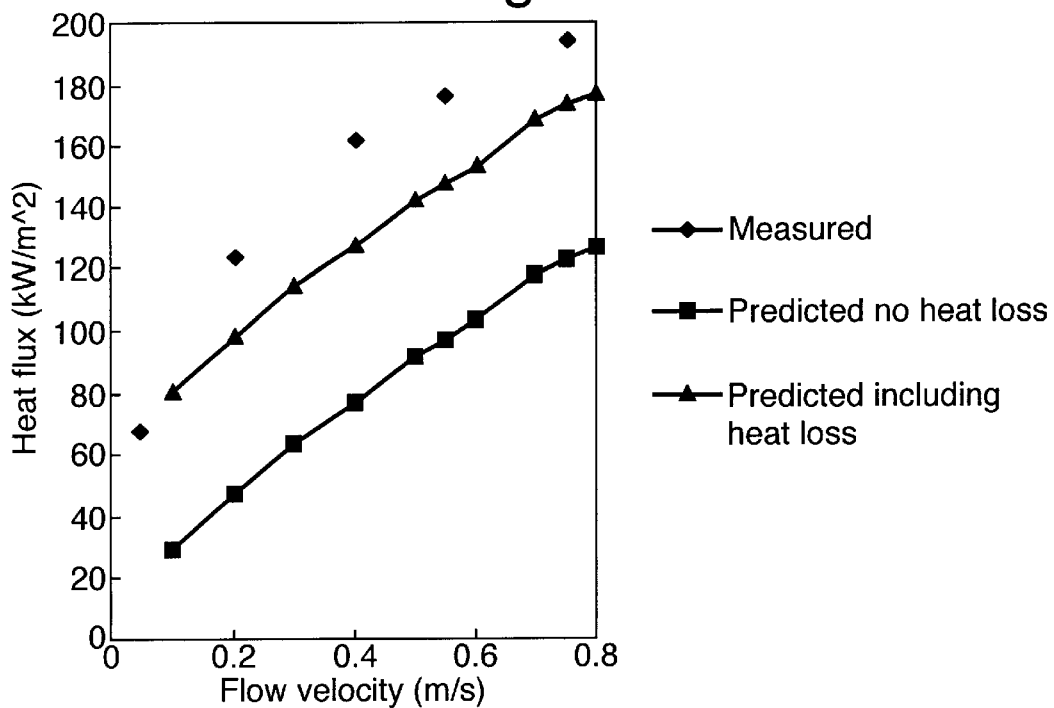

FIG. 6 shows how the heat losses from the Jones et al heat flux sensor affect the results obtained. The measured results indicate that, even taking into account some heat loss in the predicted results, there were more heat losses from the sensor than were allowed for. Thus the Jones et al sensor would not provide reliable results if used commercially.

There is therefore a need for an improved monitoring apparatus which can monitor a soil build-up on the interior of a fluid conduit adjacent to the monitoring apparatus and which is representative of the soil conditions within the conduit system.

DEFINITION OF THE INVENTION

According to a first aspect of the invention, there is provided a monitoring apparatus for monitoring soil build-up in a conduit through which fluid may flow, which apparatus includes a body located outside of the conduit and in thermal connection with it such that heat can flow between the body and the fluid flow, a heat controlling means to regulate the temperature of the body and a monitor capable of monitoring any change in power input to the heat controlling means necessary to maintain the body at the regulated temperature, whereby a change in power input to the heat controlling means is indicative of a change in heat flux between the fluid flow and the body, thereby indicating a change in soil build-up.

A second aspect of the invention provides a monitoring apparatus for monitoring soil build-up in a conduit through which fluid may flow, which apparatus includes a body in thermal connection with the conduit such that heat can flow between the body and the fluid flow; a heater for heating the body; a controller for controlling the heater; pressure measurement means to measure the fluid pressure within the conduit; and a monitor capable of monitoring the temperature of the body, the heater being controlled such that it intermittently heats the body to a predetermined temperature and the monitor being capable of monitoring the loss of heat from the body to the fluid flow, whereby a change in the rate of heat loss from the body or a change of pressure within the conduit or both is indicative of a change in soil build-up.

A third aspect of the invention provides a monitoring apparatus for monitoring soil build-up in a conduit through which fluid may flow, which apparatus includes a body in thermal connection with the conduit such that the body is at a lower temperature than the fluid flow and heat can flow from the fluid flow to the body, means for cooling the body and a monitor capable of monitoring heat flux from the fluid flow to the body whereby a change in heat flux from the fluid flow to the body is indicative of a change in soil build-up.

A fourth aspect of the invention provides a method of operating a pipework system, the method including monitoring soil build-up in the pipework system using a monitoring apparatus according to the first, second or third aspects of the present invention.

DETAILED DESCRIPTION OF THE INVENTION

The monitoring apparatus of the invention is capable of utilizing the principle of measuring the power required preferably to maintain the body at a desired temperature and from this calculating heat flux between the body and the fluid flow. Thus the heat flux is calculated from the power input to the heat controlling means rather than, as in the prior art, an indication of the heat flux based on a voltage output from a heat flux sensor. The measurement of power input to the heat controlling means has a substantial impact on the response of the sensor as well as the reproducibility of the sensor under constant flow conditions. The measurement of power in the form of watts (10-100 W) rather than microvolts (400-1000 $\mu V$) results in the sensitivity of the monitoring apparatus being much improved with the heat flux ratio (clean/dirty) now approximately 4 to 1.

The location of the monitoring apparatus body outside of the conduit has several advantages. For example, the monitoring apparatus may be non-invasive, it will not disrupt or affect the fluid flow through the conduit and it provides a more versatile arrangement in that the monitoring apparatus may quickly and easily be moved from one conduit to a different conduit without having to stop, albeit temporarily, the fluid flow through the conduit to remove the monitoring apparatus body from the conduit.

The conduit is preferably heat conductive, at least at the portion of the conduit which is adjacent the body.

The heat controlling means optionally includes a heater. Alternatively, the heat controlling means includes a cooling means.

The monitoring apparatus preferably also includes pressure measurement means to measure the fluid pressure within the conduit. Soil build-up in the conduit results in a change in both fluid pressure and heat transfer. Depending on the nature of the soil build-up, the limiting factor as regards the operational running time of a system which includes a fluid capable of generating a soil build-up in conduits of the system may be either heat transfer or pressure drop. Often in commercial systems, it is the pressure drop in the conduits of the system which is run length limiting, rather than heat transfer.

The pressure measurement means preferably includes a pressure sensor located within the conduit and a pressure monitor capable of receiving information from the sensor. The pressure monitor monitors the pressure within the conduit as measured by the pressure sensor. The monitor may indicate the pressure within the conduit to a user. The pressure sensor preferably communicates with the monitor by electrical signals or radio signals.

A monitoring apparatus which is capable of measuring both heat transfer and pressure drop in the conduit allows analysis of the soil build-up process such that it is possible to identify whether the soil is evenly distributed throughout e.g. the heat exchanger or localised within a small area of it. Knowledge of the soil distribution can be valuable in determining an appropriate cleaning strategy.

The monitoring apparatus may also include fluid flow rate measuring means and/or fluid flow temperature measuring means. The ability to measure a temperature difference between the body and the fluid flow, and/or the fluid flow rate enables the effect of variable fluid flow rate and/or variable fluid temperature to be included in the calculation of the heat flux, since the heat flux is a function of fluid flow rate and temperature driving force.

The monitoring apparatus preferably includes means for indicating the soil build-up to a user of the apparatus. More preferably, the indicating means may include a graduated scale which directly correlates to the soil build-up in the e.g. pipework system.

In a preferred embodiment, the conduit forms part of a pipework system which preferably includes a heat exchanger whereby the fluid flowing through the pipework system is heated. In such preferred embodiments the heat controlling means of the monitor apparatus preferably includes a heater. The build-up of soil in the conduit at the location of the monitoring apparatus is preferably representative of the build-up of soil in a conduit of the heat exchanger. In order to obtain representative results from the monitoring apparatus, the temperature of the body is preferably linked to the temperature of a heating medium in the heat exchanger. This will tend to result in the block temperature increasing as fouling occurs and as such the power input to the heater will also increase.

Alternatively, a higher temperature can be maintained in the body to create a "hot spot" whereby the monitoring apparatus is capable of measuring the "worst case" soil build-up.

In embodiments in which the heat controlling means includes a heater, the monitoring apparatus preferably includes insulation means to prevent heat loss from the body other than to the fluid flowing through the conduit. More preferably, the insulation means includes a guard heater to provide a source of heat to match a heat loss from the body. In a preferred embodiment, the guard heater surrounds the body and it is preferably maintained at the same temperature as the body.

By eliminating heat loss from the body other than to the fluid flowing through the conduit, true one dimensional heat transfer through the wall of the conduit can be obtained. This enables the true heat flux to be calculated.

As mentioned above, where the conduit is part of a pipework system which includes a heat exchanger, it is preferred that the soil build-up monitored by the monitoring apparatus is representative of that within the conduits which form part of the heat exchanger. Many of the heat exchangers in commercial use are of the plate heat exchanger type where the surface of the heat exchanger is corrugated. To represent soil build-up in the heat exchanger as closely as possible, the body of the monitoring apparatus preferably includes corrugations having protruding members, the protruding members of the corrugations being in thermal connection with the conduit.

In embodiments in which the heat controlling means includes a cooling means, heat is transferred from the fluid flow to the body. Such embodiments preferably include insulation means to limit heat loss from the fluid flow other than to the body. Again, eliminating heat losses allows true one dimensional heat transfer (i.e. heat flux) to be obtained.

A monitoring apparatus according to the second aspect of the invention allows the build-up of non heat-induced soils to be monitored. Such soils can occur when the fluid flowing through the conduit is e.g. toothpaste or fabric conditioner. In these cases, the soil is not subject to a temperature gradient and the imposition of a continuous heat flux would result in the conditions in the conduit adjacent to the monitoring apparatus being unrepresentative of the conditions within other parts of the conduit.

As mentioned above, in commercial systems it is often the pressure drop in the conduits of the system which is system run length limiting. Accordingly, the cleaning strategy can be based on either the depth of the soil build-up on the interior wall of the conduit or on the fluid pressure in the conduit.

Furthermore, the ability to measure both heat transfer and pressure in the conduit allows analysis of the soil build-up process such that it is possible to identify whether the soil is evenly distributed throughout e.g. the pipework system or localised within a small area of it. Knowledge of the soil distribution can be valuable in determining an appropriate cleaning strategy.

Instead of a continuous heat flux between the body and the fluid flow, the body of a monitoring apparatus according to the second aspect of the invention receives an intermittent pulse of heat energy from the heater. The monitoring means then monitors the decay of the body temperature as heat is lost to the fluid flow. Typically, the more soil on the interior surface of the conduit, the slower the heat from the body will be transferred to the fluid flow.

Preferably, the body has a low thermal mass so that the energy pulse from the heater can be short and result in a substantially instantaneous change in temperature of the body.

Preferably the monitoring apparatus determines when cleaning of the pipework system should occur. That is to say the pipework system is preferably cleaned according to the soil build-up indicated by the monitoring apparatus. More preferably the monitoring apparatus also determines the extent of cleaning required. By also monitoring the level of soil in the pipework system during cleaning, the monitoring apparatus preferably indicates when the pipe work system is sufficiently clean for normal operation of fluid flow through the pipe work system to resume. In a preferred embodiment, cleaning of the pipework system is commenced when a monitored soil level reaches a first predetermined value and cleaning is ceased when the monitored soil level is reduced to a second predetermined value.

Figure 4:
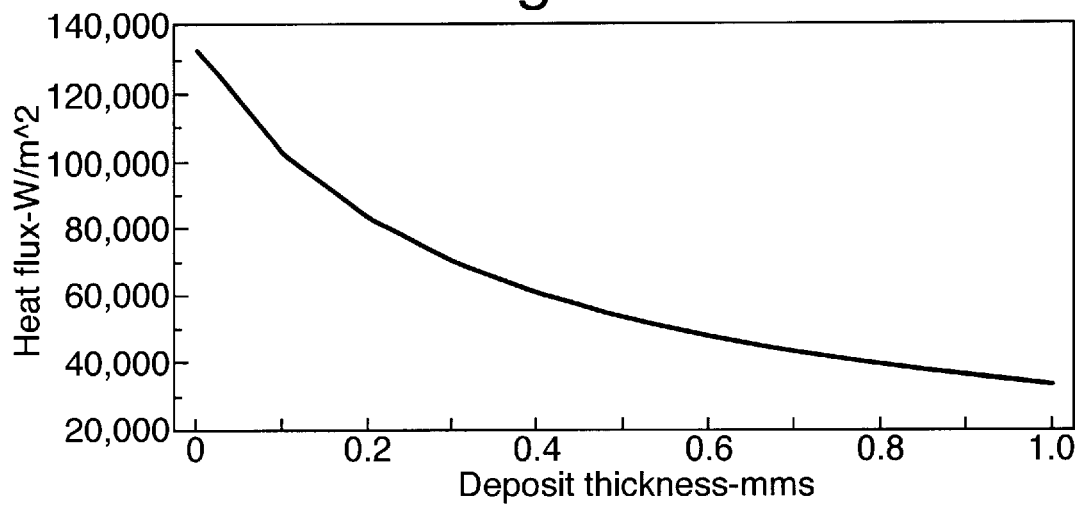
Figure 2A:
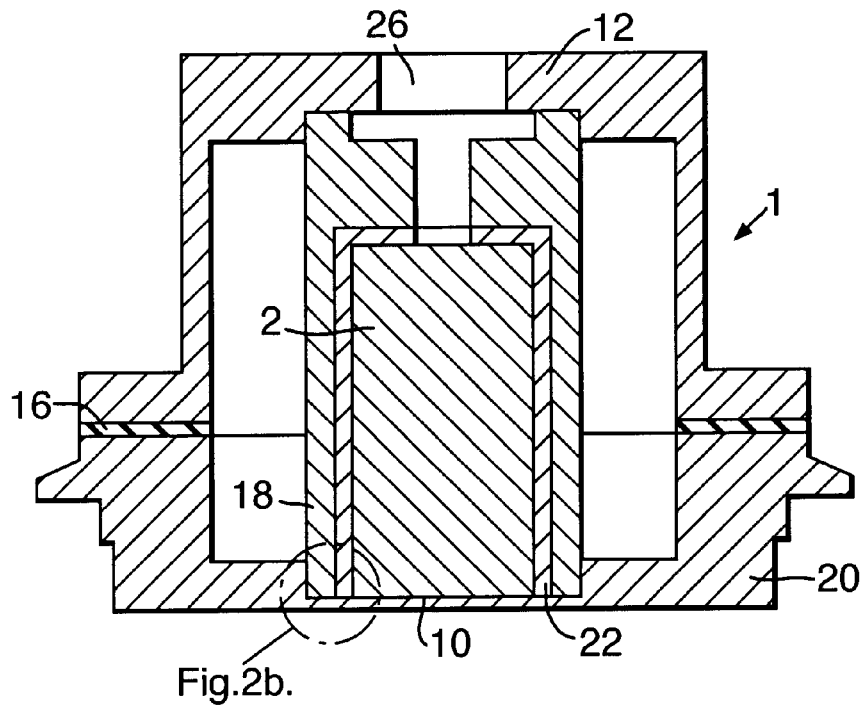
Figure 2B:
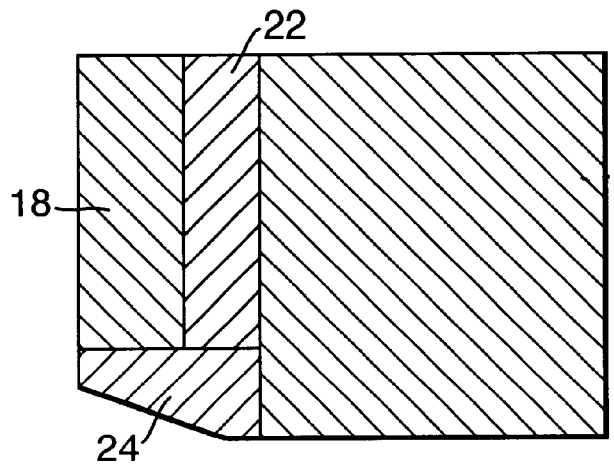
Figure 3A:
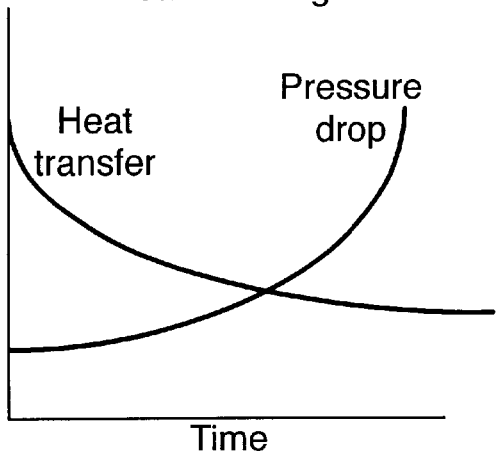
Figure 3B:
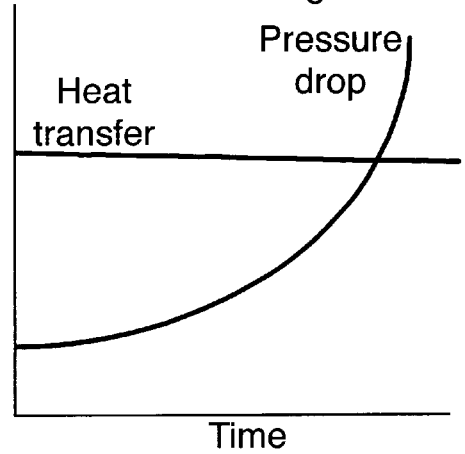
Figure 5:
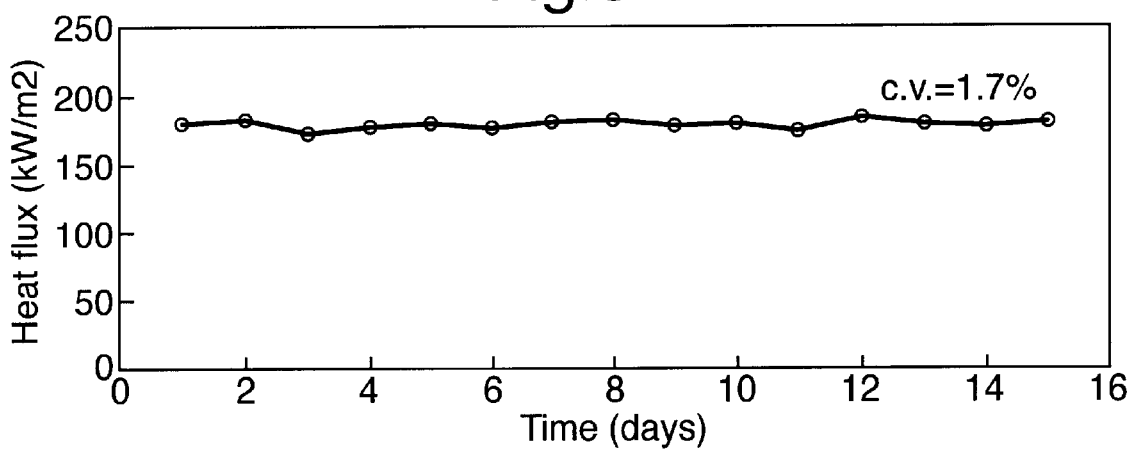

Embodiments of the invention will now be described further by way of example only, with reference to the accompanying drawings, in which:

FIG. 1 is a schematic representation of a monitoring apparatus according to the present invention attached to a pipe, FIG. 2A is a cross sectional view through a monitoring apparatus according to the present invention, FIG. 2B is an enlarged view of part of the monitoring apparatus shown in FIG. 2A, FIG. 3A is a graph showing the effects of even soil build-up within a heat exchanger on physical properties of the system, FIG. 3B is a graph showing the effects of uneven soil build-up within a heat exchanger on physical properties of the system, FIG. 4 is a graph showing the effect of increasing soil thickness on heat flux, FIG. 5 is a graph showing the reproducibility of an embodiment of the present invention under clean conditions, FIG. 6 is a graph showing the effect of heat losses on sensor response, and FIGS. 7a and 7b are schematic representations showing heat losses from a known heat flux sensor arrangement.

FIGS. 7a and 7b have already been described above.

The basic concept of the present invention is shown in FIG. 1 in which a monitoring apparatus 1 including a copper body 2 is located outside of and thermally connected to a 25 mm stainless steel (316/304 type) pipe 6 via heat transfer paste 10. The copper body 2 includes a heater (not shown) which is connected to a power supply 4 which maintains the copper body 2 at a constant temperature. Heat from the copper body 2 is transmitted through the wall 7 of pipe 6 to a milk protein solution 8 flowing through the pipework.

The heat from the copper body 2 which is transferred to the milk protein solution 8 causes soil build-up of protein material and minerals at the portion of the pipe which is in proximity to the monitoring apparatus 1. Preferably, the soil build-up generated and monitored by the monitoring apparatus 1 is representative of soil build-up in other parts of the pipe such as portions of the pipe which form part of a heat exchanger assembly.

FIG. 2 provides a more detailed representation of the monitoring apparatus 1. The copper body 2 is housed in a stainless steel housing consisting of a stainless steel cover 12 screwed to a stainless steel base 20 with a rubber gasket 16 located between the cover 12 the base 20. The copper body 2 includes a cartridge heater (not shown) and is surrounded by a peek-insulator 22. Surrounding the insulator 22 is a copper sleeve 18 housing a band heater (not shown). The copper sleeve 18 and band heater act as a guard heater to counteract any potential heat losses other than heat lost to the milk protein solution 8.

There is a layer of zinc oxide heat transfer paste 10 between the copper body 2 and the wall 7 of the copper pipe 6. This ensures optimum transfer of heat from the copper body 2 to the milk protein solution 8 flowing through pipe 6.

FIG. 2B shows an enlarged view of part of FIG. 2A showing a copper insert 24 which extends the copper sleeve 18 and guard heater to provide a heat source at the pipe wall 7 which eliminates heat losses along the pipe wall 7. This ensures true one dimensional heat transfer through the pipe wall 7.

The monitoring apparatus 1 is clamped to the pipe wall 7 by a clamp assembly (not shown). However, it will be immediately apparent to a skilled person that there are alternative arrangements for attaching the monitoring apparatus 1 to the pipe wall 7. One such alternative arrangement (not shown) is to attach the monitoring apparatus 1 to a unit which plugs into a standard pipe fitting.

Aperture 26 allows electrical wires (not shown) to connect the cartridge heater in the copper body 2 and the band heater in copper sleeve 18 to respective power sources and/or controller(s) (not shown).

The power source and controller for regulating the heater temperatures, and thus the temperature of the copper body 2 and copper sleeve 18 are well known in the art and need not be described further here.

In a further preferred embodiment of the invention, the monitoring apparatus 1 may include a pressure sensor (not shown). The pressure sensor may be any commercially available pressure sensor.

FIG. 3A relates to a pipework system for transporting milk protein solution 8 in which the pipe work system includes a heat exchanger. It shows the effect of even soil build-up within the heat exchanger on heat transfer to the milk protein solution 8 and on the pressure drop within the pipework system. It can be seen that as soil build-up increases, the heat transferred to the milk protein solution 8 decreases while the pressure drop within the system increases (i.e. the overall pressure within the. pipework system decreases).

This can be compared with FIG. 3B which relates to a similar pipework system but this time shows the effect of uneven soil build-up. It can be seen in this case that the heat transfer to a milk protein solution 8 remains constant whereas the pressure drop within the system increases. That is to say that a monitoring system which monitors both heat transfer and pressure drop provides the system operator with a better picture of the soil build-up within the heat exchanger of the pipework system.

FIG. 4 shows how the heat flux transferred to the milk protein solution 8 decreases with increasing soil thickness. It can be seen that an 0.3 mm thick soil deposit will cause the heat flux transferred to the milk protein solution 8 to be approximately half that transferred with no soil deposit on the interior of the pipe 6.

The monitoring apparatus 1 of the present invention provides a high level of reproducibility and sensitivity compared with known monitoring apparatus. The high levels of reproducibility can be seen in FIG. 5 which show the heat flux measure over 16 days (coefficient of variation {C.V.} equal to about 1.7%) using an embodiment of the invention as described above under clean conditions.

It is to be understood that while the invention has been described above in conjunction with preferred specific embodiments, the description and examples are intended to illustrate and not limit the scope of the invention which is defined by the scope of the appended claims.

What is claimed is:

1. A method of operating a pipework system, the method including monitoring soil build-up in the pipework system using a monitoring apparatus for monitoring soil build-up in a conduit through which fluid may flow, the monitoring apparatus comprising a body located outside of and in thermal connection with the conduit, such that heat can flow between the body and the fluid flow; a heat controlling means to regulate the temperature of the body; a monitor capable of monitoring any change in power input to the heat controlling means necessary to maintain the body at the regulated temperature, whereby the change in power input to the heat controlling means is indicative of a change in heat flux between the fluid flow and the body, thereby indicating a change in soil build-up, said method comprising the steps of measuring the power input required to maintain the body at a desired temperature, and calculating the heat flux between the fluid flow and the body using the power input.

2. The method according to claim 1 wherein the pipework system is cleaned according to the soil build-up indicated by the monitoring apparatus.

3. The method according to claim 1, wherein cleaning is commenced when a monitored soil level reaches a first predetermined value and cleaning is ceased when the monitored soil level is reduced to a second predetermined value.

4. The method according to claim 1, wherein the said soil build-up is milk protein from a milk protein solution.

* * * * *